(12) United States Patent
Hwang

(10) Patent No.: US 7,635,335 B2
(45) Date of Patent: Dec. 22, 2009

(54) DEVICE FOR MOVING A TRANSDUCER OF AN ULTRASONIC PROBE

(75) Inventor: Won Soon Hwang, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 715 days.

(21) Appl. No.: 11/266,325

(22) Filed: Nov. 4, 2005

(65) Prior Publication Data
US 2007/0016060 A1    Jan. 18, 2007

(30) Foreign Application Priority Data
Jul. 15, 2005    (KR)    ....................... 10-2005-0064257

(51) Int. Cl.
*A61B 8/14* (2006.01)
(52) U.S. Cl. ................. 600/459; 600/437; 600/462; 310/317; 310/319; 73/633
(58) Field of Classification Search .................. 73/618, 73/625, 635, 636; 600/437, 444, 447, 459; 310/317, 319
See application file for complete search history.

(56) References Cited
U.S. PATENT DOCUMENTS

| 4,120,291 A | 10/1978 | Paton et al. |
| 4,346,867 A | 8/1982 | Dick et al. |
| 4,681,120 A | 7/1987 | Kunii |
| 4,930,515 A * | 6/1990 | Terwilliger .................. 600/462 |
| 5,460,179 A * | 10/1995 | Okunuki et al. ............. 600/444 |

FOREIGN PATENT DOCUMENTS

| JP | 11-2069 | 1/1999 |
| JP | 2004-290272 | 10/2004 |

OTHER PUBLICATIONS

U.S. Appl. No. 11/267,507, filed Nov. 7, 2005, Hwang.

* cited by examiner

*Primary Examiner*—Brian Casler
*Assistant Examiner*—John F Ramirez
(74) *Attorney, Agent, or Firm*—Oblon, Spivak, McClelland, Maier & Neustadt, L.L.P.

(57) ABSTRACT

The present invention relates to a device for moving a transducer of an ultrasonic probe in an ultrasonic diagnostic apparatus for acquiring a 3-dimensional ultrasound image. A motor for generating power to move the transducer and guide rails for guiding the movement of the transducer are mounted to the frame. The rotational force of a driving shaft of the motor is transmitted to a driven shaft through pulleys and belts. A portion of a wire is wound around the driven shaft and both ends of the wire are fixed to two opposing surfaces of the transducer. A reel having a spiral groove on the peripheral surface is coupled to the driven shaft. The wire is wound along the spiral groove.

10 Claims, 6 Drawing Sheets

DEVICE FOR MOVING A TRANSDUCER OF AN ULTRASONIC PROBE

FIELD OF THE INVENTION

The present invention generally relates to an ultrasonic probe, and more particularly to a device for moving a transducer of an ultrasonic probe in an ultrasonic diagnostic apparatus for acquiring a 3-dimensional ultrasound image.

BACKGROUND OF THE INVENTION

An ultrasonic diagnostic apparatus is a medical equipment for obtaining an ultrasound image of a target region in an object so as to provide clinical information of the target region, such as lesion or neoplasm information of internal organs, fetus information and the like. Typically, the ultrasonic diagnostic apparatus comprises at least one probe for radiating an ultrasonic wave to the target region and receiving an echo signal reflected from the target region. The probe has a transducer for converting an ultrasonic signal into an electric signal.

Recently, in order to obtain more accurate diagnosis, there have been developed techniques for acquiring a 3-dimensional (3D) ultrasound image by pivoting the transducer.

As shown in FIG. 5, Japanese Patent Application Publication No. 2004-290272 discloses a prior art ultrasonic probe with a device for moving a transducer. FIG. 5 is a perspective view showing a device for moving a transducer of a prior art ultrasonic probe.

As shown in the drawing, a prior art probe 1 is equipped with a frame 5 and a cover 8, which is coupled to the frame 5 and is adapted to contact an object to be examined (e.g., a body of a patient). A motor 4 for generating driving power for pivoting a transducer 2 is mounted to the frame 5. A driving arm 6 is fixed to a driving shaft of the motor 4. A holder 3 for supporting the transducer 2 is mounted to the frame 5. The holder 3 has a holding part 3a for holding the transducer 2 and a pair of swing parts 3b, which are coupled to both side-ends of the holding part 3a and mounted pivotably to the frame 5 by hinge pins 9. The holding part 3a of the holder 3 is arranged to confront the driving arm 6 and has a groove (not shown) on the surface facing the driving arm 6. The driving arm 6 has a recess (not shown) on the surface facing the holding part 3a of the holder 3. The recess is located eccentrically with the driving shaft of the motor 4. A ball (not shown) is interposed between the recess of the driving arm 6 and the groove of the holding part 3a. When the motor 4 operates and the driving shaft is rotated, the ball contained in the recess of the driving arm 6 revolves around the driving shaft. At the same time, the ball rolls along the groove of the holding part 3a to thereby pivot the holder 3 holding the transducer 2 on the hinge pins 9.

However, in the above prior art device that moves the transducer of the ultrasonic probe, the rotation angle of the driving shaft of the motor, which is determined by the duration of a pulse, directly influences the pivot angle of the transducer through the driving arm and the holder. Thus, the transducer moves somewhat roughly and the ultrasonic wave is radiated irregularly. As such, the image quality becomes degraded, which can cause an erroneous diagnosis. Although a high-precision motor may be provided in order to resolve this problem, it causes a considerable increase in manufacturing costs.

Also, the radius of rotation of the transducer is determined by the length of the swing part of the holder. Thus, when manufacturing the probe having a relatively large radius of rotation of the transducer, the probe may be enlarged ineffectively or the limited size of the probe may impose many undesired limitations upon installing the long holder.

SUMMARY OF THE INVENTION

It is an object of the present invention to provide a device for moving a transducer of an ultrasonic probe, which can move the transducer smoothly to radiate the ultrasonic wave regularly, thereby achieving a high image quality.

It is another object of the present invention to provide a device for moving a transducer of an ultrasonic probe, which facilitates the manufacturing of the probes having different radii of rotation of the transducers without changing the overall size of the probes.

In accordance with an aspect of the present invention, there is provided a device for moving a transducer of an ultrasonic probe, wherein the probe includes a case and a transducer for alternately converting an ultrasonic signal into an electric signal. The device comprises: a frame mounted inside the case; a motor mounted to the frame and having a driving shaft; a driven shaft rotatably mounted to the frame; guide rails mounted to the frame for guiding the movement of the transducer; means for transmitting the rotational force of the driving shaft to the driven shaft; and means for transmitting the rotational force of the driven shaft to the transducer to move the transducer along the guide rails.

The transducer is positioned between the guide rails and is provided with bearings at the surfaces facing the guide rails. Slots are formed lengthwise at the guide rails so that the bearings are received in the slots and roll on the slots.

The means for transmitting the rotational force of the driving shaft to the driven shaft consists of pulleys and belts wound around the pulleys in order to connect them. Teeth are formed at the pulleys and the belts so that they can be tooth-engaged with each other.

The means for transmitting the rotational force of the driven shaft to the transducer is a wire. A portion of the wire is wound around the driven shaft and both ends of the wire are fixed to two opposing surfaces of the transducer.

A reel having a spiral groove on the peripheral surface is coupled to the driven shaft. The wire is wound along the spiral groove.

The device further comprises means for maintaining the tension of the wire in a uniform manner. Preferably, the means are elastic members fixed to two opposing surfaces of the transducer. The ends of the wire are connected to the ends of the elastic members.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PRESENT INVENTION

Figure 1:
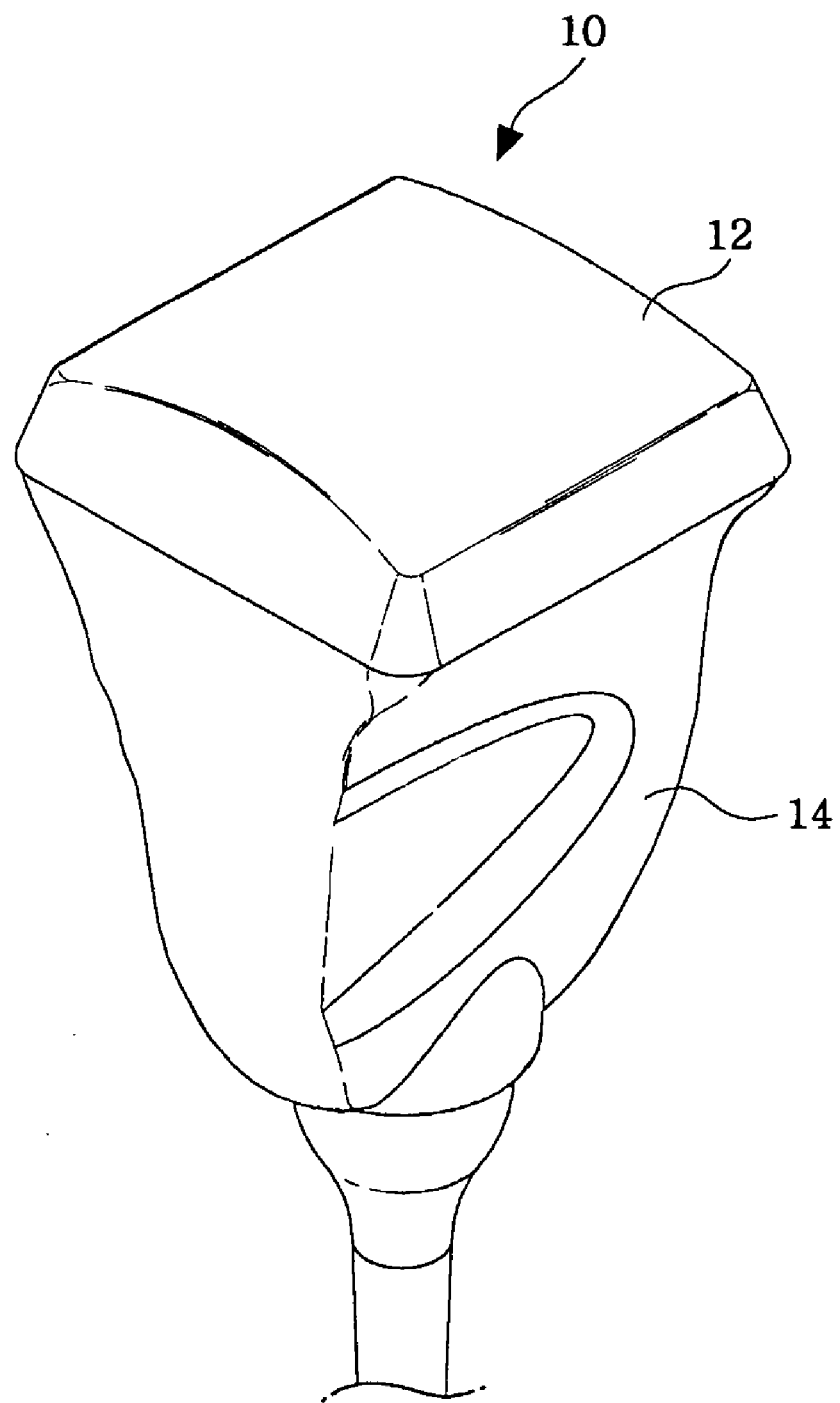
FIG. 1 is a perspective view showing an outer appearance of an ultrasonic probe constructed in accordance with the present invention.
Figure 2:
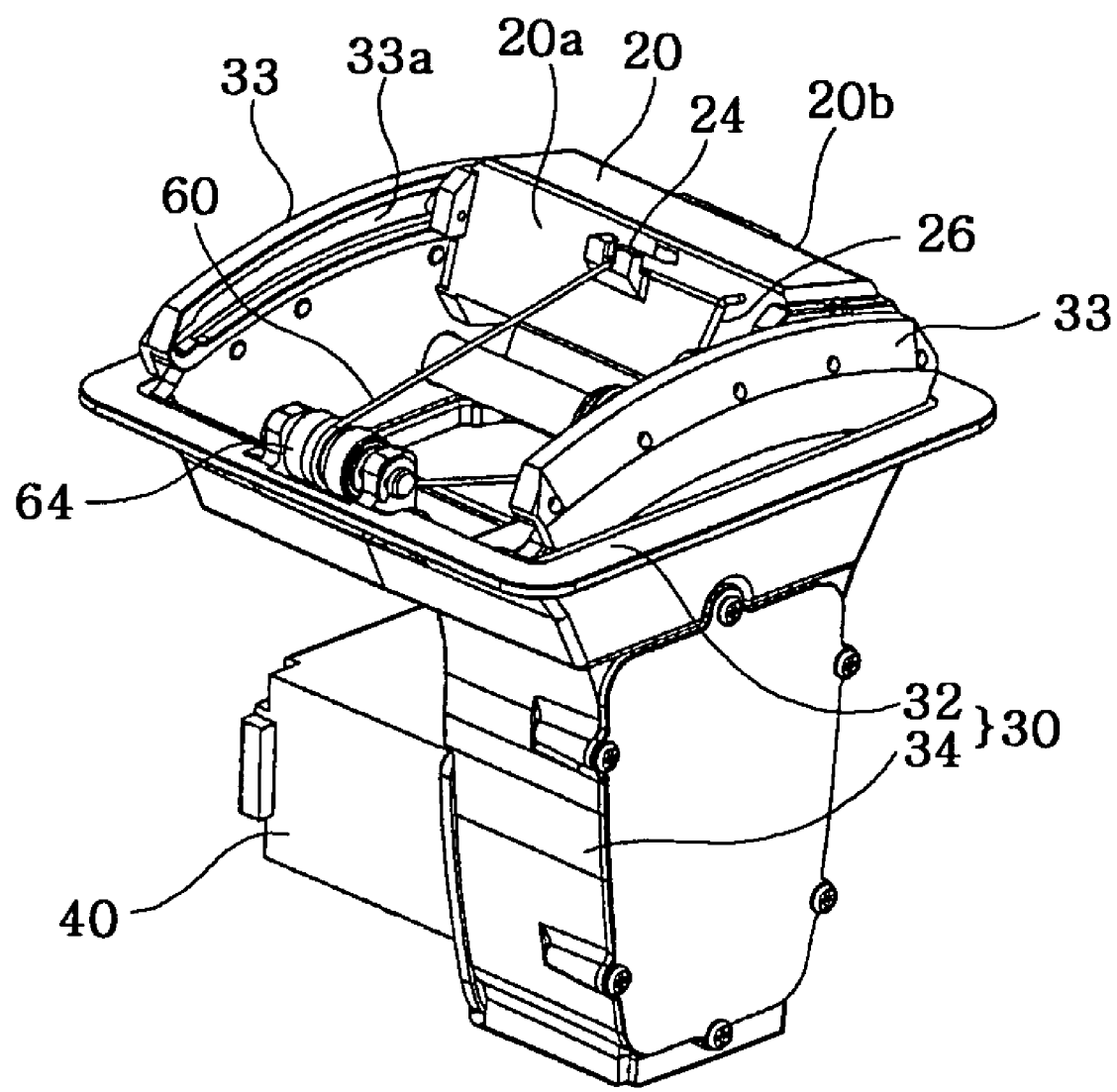
FIG. 2 is a perspective view showing an inner structure of an ultrasonic probe constructed in accordance with the present invention.
Figure 3:
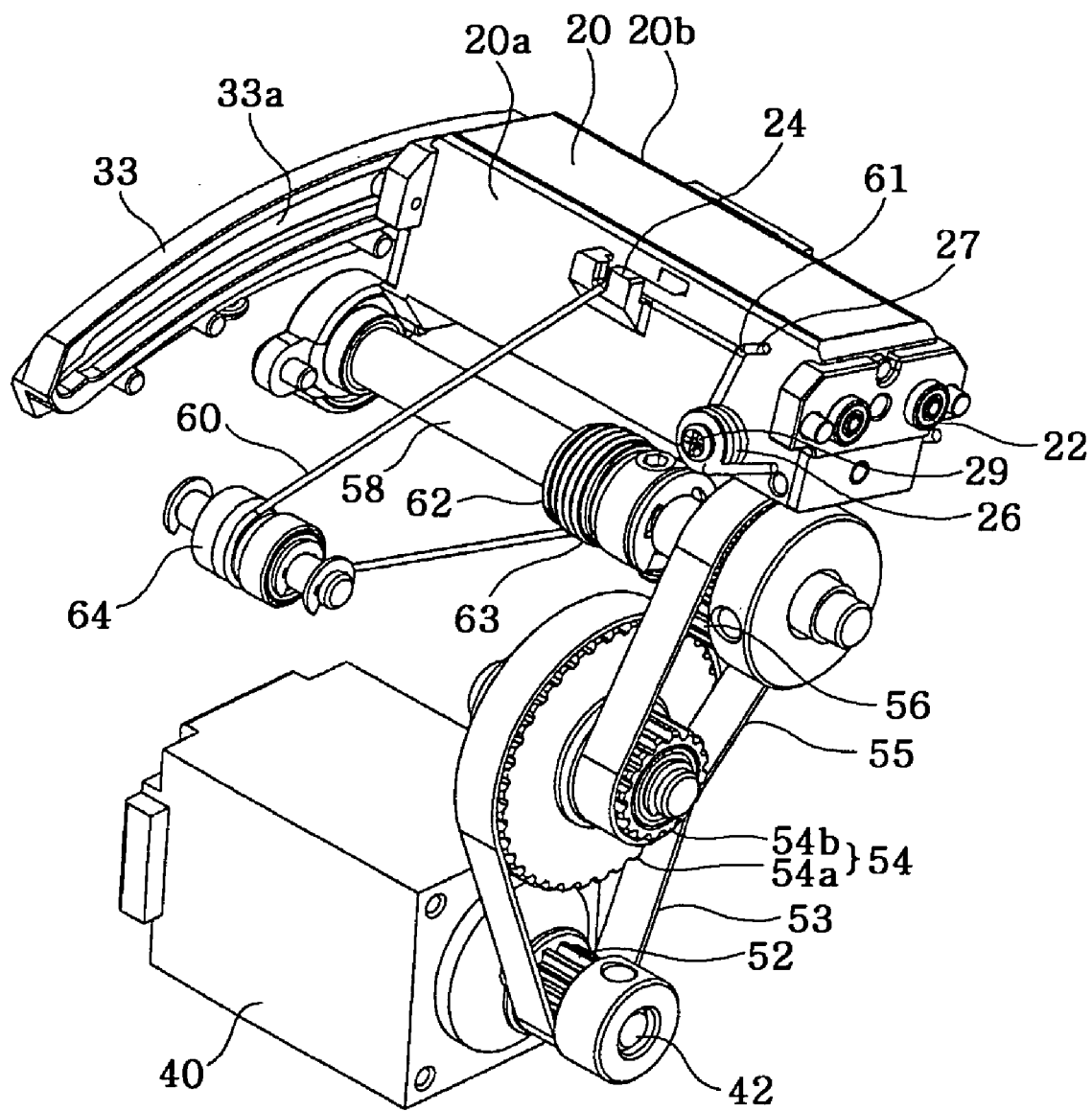
FIG. 3 is a perspective view showing a device for moving a transducer of an ultrasonic probe constructed in accordance with the present invention.

FIGS. 1 and 2 are perspective views showing an outer appearance and an inner structure of an ultrasonic probe constructed in accordance with the present invention, respectively. FIG. 3 is a perspective view showing a device for moving a transducer of an ultrasonic probe, which is constructed in accordance with the present invention.

As shown in the drawings, an ultrasonic probe 10 comprises a case 14 having an opened top and a cover 12, which is coupled to the top of the case 14 and is adapted to contact an object to be examined (e.g., a body of a patient). A frame 30 for supporting most of the essential components of the probe is contained in the case 14. A transducer 20 for alternately converting an ultrasonic signal into an electric signal is movably mounted to the frame 30.

The frame 30 includes a rectangular supporting part 32 and a receiving part 34, which is formed integrally below the supporting part 32. The supporting part 32 has a pair of guide rails 33 on its opposing verges. Slots 33a are formed lengthwise at the opposing side surfaces of the guide rails 33. The transducer 20 is positioned between the pair of guide rails 33. Bearings 22 are mounted to the both side-ends of the transducer 20. The bearings 22 are received in the slots 33a and roll along the slots 33a. The slot 33a may be formed in a convex, linear or concave shape.

A motor 40 for generating power for moving the transducer 20 and means for transmitting the power from the motor 40 to the transducer 20 are mounted to the frame 30. Preferably, the motor 40 is a step motor. This is because the step motor is low in cost and highly reliable, as well as having high torque at low speeds and a simple, rugged construction that operates in almost any environment. A driving shaft 42 of the motor 40 is located inside the receiving part 34 of the frame 30 by passing through the side wall of the receiving part 34.

As shown in FIG. 3, a driving pulley 52 is coupled to the driving shaft 42 of the motor 40. An intermediate pulley 54 is located above the driving pulley 52 and a driven pulley 56 is located above the intermediate pulley 54. The intermediate pulley 54 includes a first pulley 54a and a second pulley 54b, which is coupled concentrically to the first pulley 54a. The driving pulley 52 and the first pulley 54a of the intermediate pulley 54 are connected by a timing belt 53 to interlock with each other. The second pulley 54b of the intermediate pulley 54 and the driven pulley 56 are connected by a timing belt 55 to interlock with each other. Teeth are formed at the pulleys 52, 54 and 56 and the timing belts 53 and 55 so as to prevent any slip therebetween. The driving pulley 52, the intermediate pulley 54 and the driven pulley 56 all have predetermined diameters for an adequate speed reduction ratio to move the transducer 20.

A driven shaft 58 is fixed to the center of the driven pulley 56 at its one end so as to be rotated together with the driven pulley 56. The other end of the driven shaft 58 is rotatably mounted to the side wall of the supporting part 32 of the frame 30. The driven shaft 58 is arranged parallel with the transducer 20.

A reel 62 is coupled to the driven shaft 58 so as to be rotated together therewith in such a manner that the driven shaft 58 is fitted through the center of the reel 62. A spiral groove 63 is formed on the peripheral surface of the reel 62. A wire 60 is wound around the reel 62 along the spiral groove 63. Therefore, when the driven shaft 58 and the reel 62 are rotated, any slip and entanglement of the wire 60 can be prevented. The speed reduction ratio, which is adequate for the movement of the transducer 20, can be adjusted by changing the diameter of the reel 62 as well as the pulleys 52, 54 and 56.

A pair of rollers 64 is rotatably mounted on the opposing verges of the supporting part 32 of the frame 30. The rollers 64 are arranged such that the rotation axis of the roller 64 is parallel with that of the driven shaft 58. One end portion of the wire 60 extending from the reel 62 proceeds toward a front surface 20a of the transducer 20 via one of the rollers 64, while the other end portion of the wire 60 extending from the reel 62 proceeds toward a rear surface of 20b of the transducer 20 via the other roller 64.

On the front and rear surfaces 20a and 20b of the transducer 20, there are provided hooks 24 and wire-tensioning means 26. Both end portions of the wire 60 are hitched by the hooks 24 and then connected to the wire-tensioning means 26. Preferably, the wire-tensioning means 26 is an elastic member such as a torsion coil spring. The torsion coil springs 26 are fixed to the front and second surfaces 20a and 20b of the transducer 20 by means of screws 29 or the like. To connect the wire 60 to the torsion coil springs 26, knot portions 61 are formed at both ends of the wire 60 and L-shaped bending portions 27 are formed at the ends of the torsion coil springs 26. The knot portion 61 of the wire 60 is hitched by the bending portion 27 of the torsion coil spring 26.

Hereinafter, the operational effect of the device for moving the transducer of the ultrasonic probe, which is constructed in accordance with the present invention, will be described with reference to FIGS. 4a and 4b.

Figure 4A:
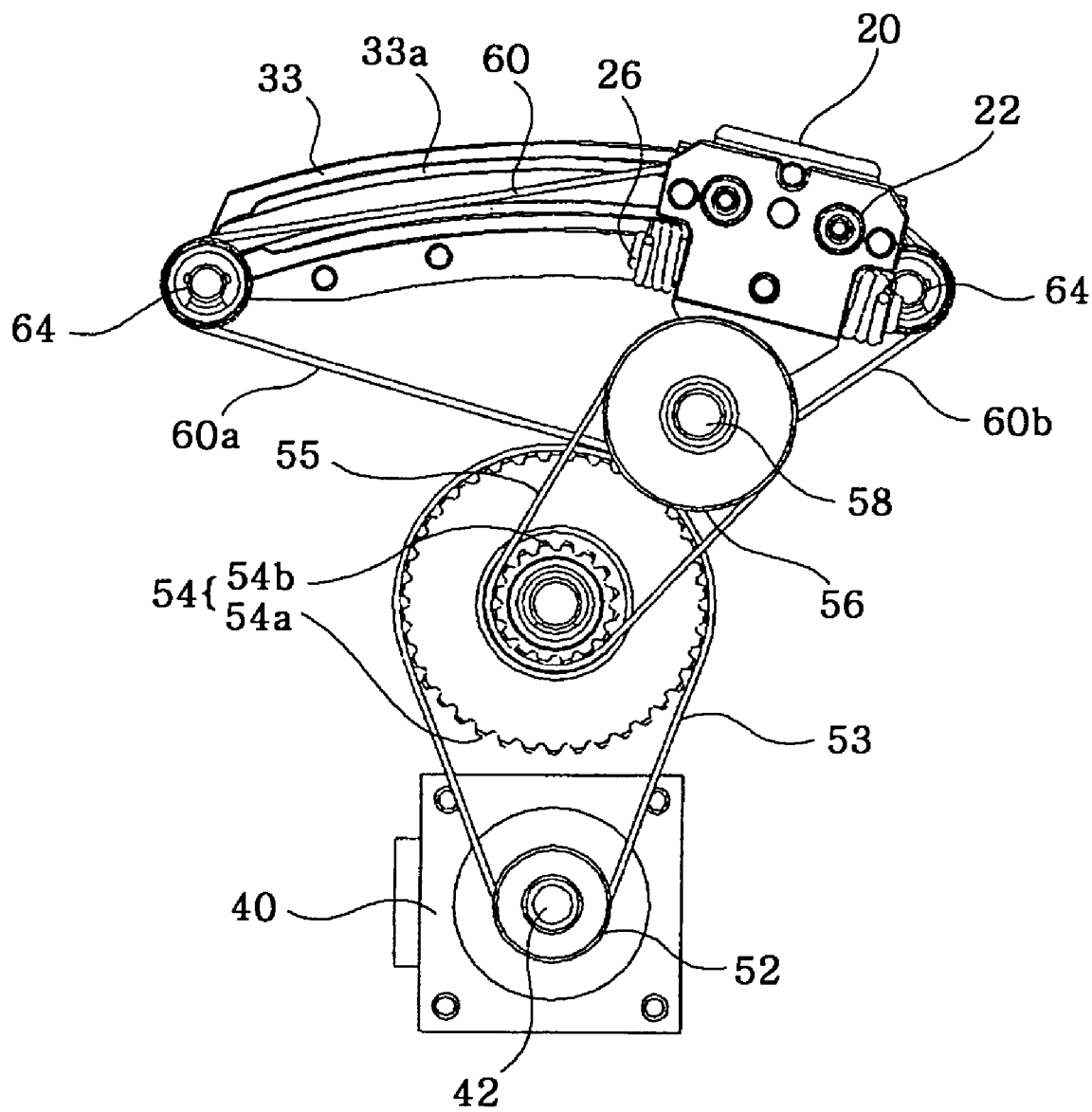
FIG. 4a is a side view showing an operating state of a device for moving a transducer of an ultrasonic probe constructed in accordance with the present invention.
Figure 4B:
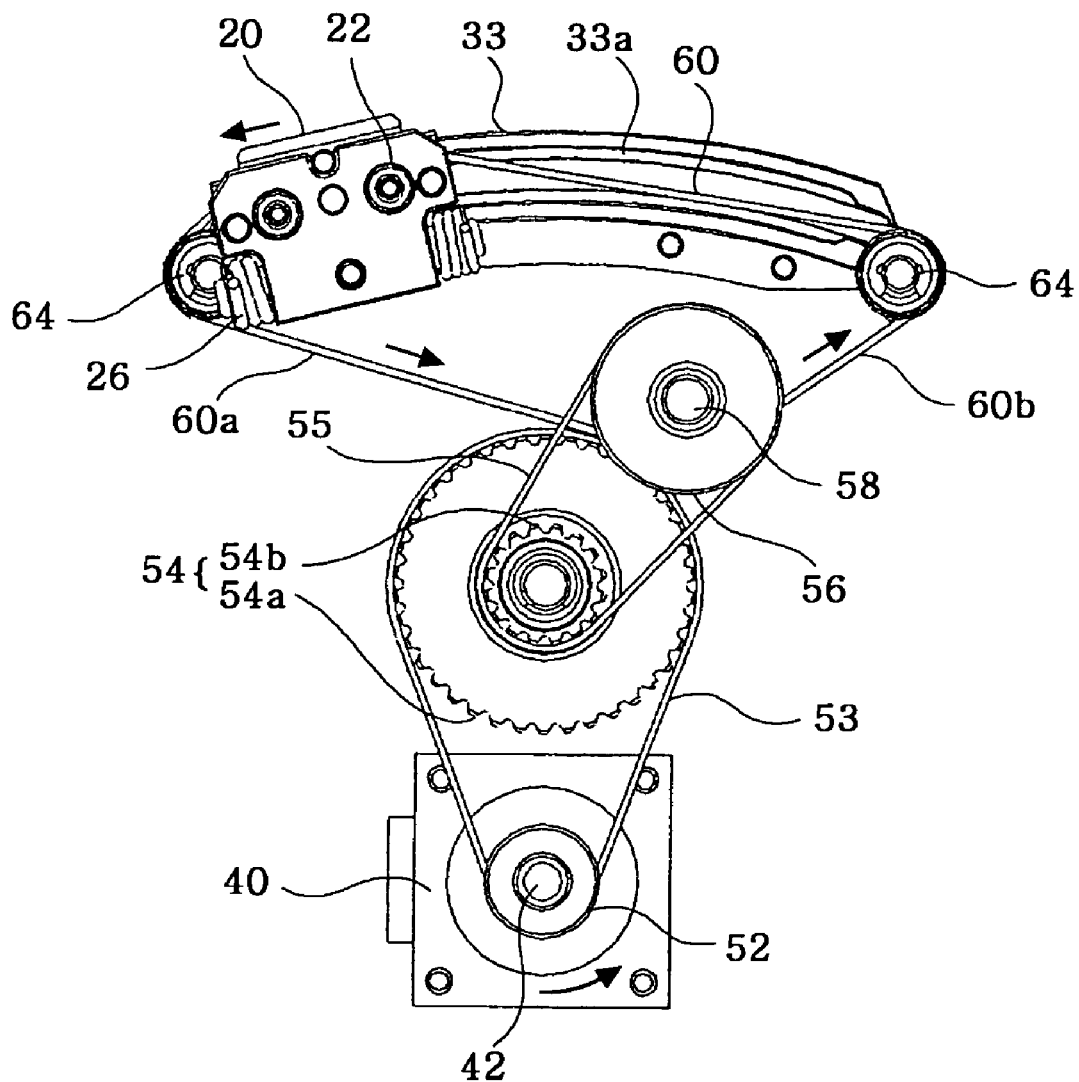
FIG. 4b is a side view showing another operating state of a device for moving a transducer of an ultrasonic probe constructed in accordance with the present invention.
Figure 5:
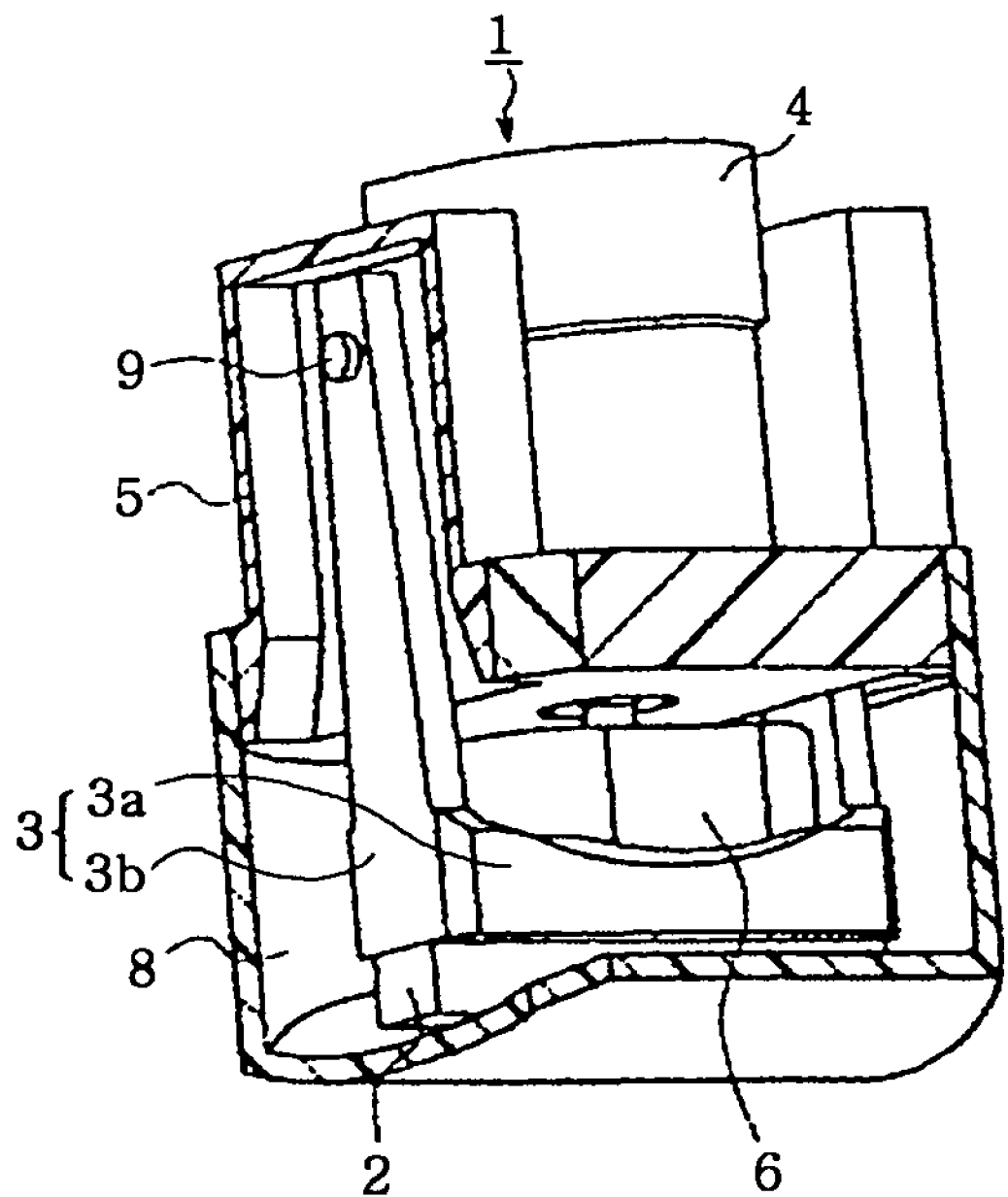
FIG. 5 is a perspective view showing a device for moving a transducer of a prior art ultrasonic probe.

First, it is defined as an initial state that the transducer 20 is located at the rightmost side of the guide rails 33 (as shown in FIG. 4a). In such an initial state, if the motor 40 operates to rotate the driving shaft 42 in a direction of arrow shown in FIG. 4b, the driving pulley 52 coupled to the driving shaft 42, the intermediate pulley 54 connected to the driving pulley 52 through the timing belt 53, and the driven pulley 56 connected to the intermediate pulley 54 through the timing belt 55 are rotated together. At the same time, the driven shaft 58, which is coupled to the driven pulley 56, is also rotated. Then, a first portion 60a of the wire 60, which is located at the left of the driven shaft 58 (as shown in FIG. 4b), gets coiled around the reel 62 along the spiral groove 63, while a second portion 60b of the wire 60, which is located at the right of the driven shaft 58 (as shown in FIG. 4b), gets released from the reel 62. By such movement of the wire 60, the transducer 20 moves in a direction of arrow shown in FIG. 4b along the slots 33a of the guide rails 33. The transducer 20 can move smoothly by the bearings 22 rolling on the slots 33a. Since both ends of the wire 60 are connected to the wire-tensioning means, i.e., the torsion coil springs 26 fixed to the transducer 20, the tension of the wire 60 can be uniformly maintained during repeated operations, thereby enhancing the operational reliability.

By the aforesaid driving mechanism, the transducer 20 can perform the reciprocating motions along the slots 33a of the guide rail 33 so as to acquire a 3D ultrasound image of a target region in an object. Since a device and a method for detecting the position of the transducer 20 and controlling the motor 40 are already well known in the art, the explanation thereof is omitted herein.

As described above, the speed reduction ratio for adequately moving the transducer to the rotation angle of the driving shaft of the motor can be easily achieved by the pulleys, the reel and the wire within the limited size of the probe. Thus, the moving precision of the transducer can be increased and the ultrasonic wave can be radiated regularly. Accordingly, the process of obtaining a 3D ultrasound image can be performed smoothly and continuously, thereby increasing the image quality and reducing errors in diagnosis.

Also, although the wire itself may get loosened due to repeated operations, the tension of the wire is uniformly maintained by the restoring force of the torsion coil springs, thereby enhancing the operational stability and reliability.

Also, by merely modifying the curvature of the slot of the guide rail, various types of probes with a movable transducer can be easily manufactured without changing the overall size of the probe.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. A device for moving a transducer of an ultrasonic probe, the probe including a case and a transducer for converting an ultrasonic signal into an electric signal, the device comprising:
   a frame mounted inside the case;
   a motor mounted to the frame and having a driving shaft;
   a driven shaft rotatably mounted to the frame;
   guide rails mounted to the frame for guiding the movement of the transducer;
   means for transmitting a rotational force of the driving shaft to the driven shaft; and
   means for transmitting a rotational force of the driven shaft to the transducer to move the transducer along the guide rails,
   wherein the means for transmitting the rotational force of the driven shaft to the transducer is a wire, and wherein a portion of the wire is wound around the driven shaft and the ends of the wire are fixed to two opposing surfaces of the transducer,
   wherein a reel having a spiral groove on the peripheral surface is coupled to the driven shaft,
   and wherein the wire is wound along the spiral groove.

2. The device as recited in claim 1, wherein the transducer is positioned between the guide rails and is provided with bearings at the surfaces facing the guide rails, and
   wherein slots are formed lengthwise at the guide rails,
   whereby the bearings are received in the slots and roll on the slots.

3. The device as recited in claim 1, wherein the means for transmitting the rotational force of the driving shaft to the driven shaft consists of pulleys and belts wound around the pulleys to connect them.

4. The device as recited in claim 3, wherein teeth are formed at the pulleys and the belts so that they are tooth-engaged with each other.

5. The device as recited in claim 1, wherein the device further comprises means for uniformly maintaining the tension of the wire.

6. The device as recited in claim 5, wherein the means for uniformly maintaining the tension of the wire are elastic members fixed to two opposing surfaces of the transducer,
   and wherein the ends of the wire are connected to the ends of the elastic members.

7. The device as recited in claim 1, wherein rollers are mounted to the frame for guiding the movement of the wire.

8. A device for moving a transducer of an ultrasonic probe, the probe including a case and a transducer for converting an ultrasonic signal into an electric signal, the device comprising:
   a frame mounted inside the case;
   a motor mounted to the frame and having a driving shaft;
   a driven shaft rotatably mounted to the frame;
   guide rails mounted to the frame for guiding the movement of the transducer;
   means for transmitting a rotational force of the driving shaft to the driven shaft; and
   means for transmitting a rotational force of the driven shaft to the transducer to move the transducer along the guide rails,
   wherein the means for transmitting the rotational force of the driven shaft to the transducer is a wire, and wherein a portion of the wire is wound around the driven shaft and the ends of the wire are fixed to two opposing surfaces of the transducer, and
   wherein the device further comprises means for uniformly maintaining the tension of the wire.

9. The device as recited in claim 8, wherein the means for uniformly maintaining the tension of the wire are elastic members fixed to two opposing surfaces of the transducer,
   and wherein the ends of the wire are connected to the ends of the elastic members.

10. A device for moving a transducer of an ultrasonic probe, the probe including a case and a transducer for converting an ultrasonic signal into an electric signal, the device comprising:
    a frame mounted inside the case;
    a motor mounted to the frame and having a driving shaft;
    a driven shaft rotatably mounted to the frame;
    guide rails mounted to the frame for guiding the movement of the transducer;
    means for transmitting a rotational force of the driving shaft to the driven shaft; and
    means for transmitting a rotational force of the driven shaft to the transducer to move the transducer along the guide rails,
    wherein the means for transmitting the rotational force of the driven shaft to the transducer is a wire, and wherein a portion of the wire is wound around the driven shaft and the ends of the wire are fixed to two opposing surfaces of the transducer, and
    wherein rollers are mounted to the frame for guiding the movement of the wire.

* * * * *